(12) United States Patent
Crothers et al.

(10) Patent No.: US 10,184,813 B2
(45) Date of Patent: Jan. 22, 2019

(54) SYSTEM AND METHOD FOR PERFORMING AN AUTOMATED INSPECTION OPERATION

(71) Applicant: The Boeing Company, Chicago, IL (US)

(72) Inventors: Phillip J. Crothers, Hampton East (AU); Kurtis S. Willden, Kent, WA (US)

(73) Assignee: The Boeing Company, Chicago, IL (US)

( * ) Notice: Subject to any disclaimer, the term of this patent is extended or adjusted under 35 U.S.C. 154(b) by 247 days.

(21) Appl. No.: 15/347,454

(22) Filed: Nov. 9, 2016

(65) Prior Publication Data

US 2018/0128657 A1    May 10, 2018

(51) Int. Cl.
| | | |
|---|---|---|
| *G01N 29/22* | (2006.01) | |
| *G01D 11/30* | (2006.01) | |
| *G01N 25/72* | (2006.01) | |
| *G01N 29/04* | (2006.01) | |
| *G01N 29/265* | (2006.01) | |

(52) U.S. Cl.
CPC ............ *G01D 11/30* (2013.01); *G01N 25/72* (2013.01); *G01N 29/04* (2013.01); *G01N 29/225* (2013.01); *G01N 29/265* (2013.01)

(58) Field of Classification Search
CPC ...... G01N 25/00–25/72; G01N 29/225; H02K 41/02–41/06; G01D 11/30
USPC ... 73/618–626, 866.5, 865.8, 159, 104, 105; 348/82–96, 107, 125–134, 142; 396/419, 396/428; 33/556, 558; 324/228–243
See application file for complete search history.

(56) References Cited

U.S. PATENT DOCUMENTS

| | | | | |
|---|---|---|---|---|
| 5,860,208 | A | * | 1/1999 | Nomura ............. H05K 13/0061 29/712 |
| 6,439,096 | B1 | | 8/2002 | Mungalov et al. |
| 7,135,827 | B1 | | 11/2006 | Lampson |
| 7,148,590 | B1 | | 12/2006 | Lampson |
| 2011/0076118 | A1 | * | 3/2011 | Kurita ............... H01L 21/67259 414/217 |

(Continued)

FOREIGN PATENT DOCUMENTS

WO    WO-2014/143917 A1    9/2014

OTHER PUBLICATIONS

C. Elbuke, et al; "Design of floating micro-electro-mechanical (MEMS) systems" 2016; https://uwaterloo.ca/maglev-microrobotics-laboratory/research/design-floating-micro-electro-mechanical-mems-systems.

(Continued)

*Primary Examiner* — Robert R Raevis
(74) *Attorney, Agent, or Firm* — Miller, Matthias & Hull LLP

(57) ABSTRACT

An inspection apparatus for performing an automated inspection operation across a surface of a workpiece is disclosed. The inspection apparatus may include a platen fabricated from a magnetic material and having a platen surface, and an inspection module disposed on the platen surface and having an inspection end effector. The inspection module may generate a magnetic field that biases the inspection module toward the platen, and may be operable to generate a magnetic flux to control movement of the inspection module over the platen surface to perform the automated inspection operation across the surface of the workpiece.

20 Claims, 8 Drawing Sheets

(56) References Cited

U.S. PATENT DOCUMENTS

2015/0153312 A1* 6/2015 Gonzalez ................ G01D 5/00
                                                         73/23.2
2016/0072419 A1* 3/2016 Yamada ............... H02K 41/031
                                                         318/135

OTHER PUBLICATIONS

Scott Ellerthorpe; "Linear motors step out"; Aug. 1, 2000; http://machinedesign.com/linear-motion/linear-motors-step-out.

* cited by examiner

SYSTEM AND METHOD FOR PERFORMING AN AUTOMATED INSPECTION OPERATION

TECHNICAL FIELD

The present disclosure relates generally to performing non-destructive inspections (NDIs) on workpieces and, more particularly, to methods and systems for automating inspection operations using inspection end effectors mounted on linear motors to traverse and perform the inspection operations on surfaces of the workpieces.

BACKGROUND

Many structures, such as but not limited to components of aircraft, have inspection operations, such as visual inspection, sonographic inspections, thermographic inspection, radiographic inspections and the like, performed thereon at least in part as manual or semi-automated processes. Skilled operators, such as videographers and inspectors, can perform these operations with relatively high degrees of quality and accuracy. However, such manual processing can have inherent limits in terms of performance criteria such as time to completion of each operation, accuracy in inspecting the entire surface of the workpiece, and maintaining quality in the identification of defects in the workpiece.

SUMMARY OF THE DISCLOSURE

In one aspect of the present disclosure, an inspection apparatus for performing automated inspection operations across a surface of a workpiece is disclosed. The inspection apparatus includes a platen fabricated from a magnetic material and having a platen surface, and a first inspection module disposed on the platen surface and having a first inspection end effector. The first inspection module generates a first magnetic field that biases the first inspection module toward the platen, and is operable to generate a first magnetic flux to control movement of the first inspection module over the platen surface to perform a first automated inspection operation across the surface of the workpiece.

In another aspect of the present disclosure, a method of performing automated inspection operations across a surface of a workpiece is disclosed. The method is implemented using a first inspection module having a first inspection end effector and being disposed on a platen surface of a platen fabricated from a magnetic material. The first inspection module generates a first magnetic field biasing the first inspection module toward the platen surface. The method includes controlling, using a first magnetic flux generated by the first inspection module, movement of the first inspection module, and performing, using the first inspection end effector, a first automated inspection operation.

In a further aspect of the present disclosure, a system for performing automated inspection operations across a surface of a workpiece is disclosed. The system includes a platen fabricated from a magnetic material and having a platen surface, a first inspection module disposed on the platen surface and having a first inspection end effector, and a first inspection module controller coupled in communication with the first inspection module. The first inspection module generates a first magnetic field that biases the first inspection module toward the platen, and is operable to generate a first magnetic flux to control movement of the first inspection module over the platen surface to perform a first automated inspection operation across the surface of the workpiece. The first inspection module controller is configured to control the first magnetic flux generated by the first inspection module to move the first inspection module over the platen surface to perform the first automated inspection operation. The system further includes a second inspection module disposed on the platen surface and having a second inspection end effector, and a second inspection module controller coupled in communication with the second inspection module. The second inspection module generates a second magnetic field that biases the second inspection module toward the platen, and is operable to generate a second magnetic flux to control movement of the second inspection module over the platen surface to perform a second automated inspection operation across the surface of the workpiece, and the second inspection module controller is configured to control the second magnetic flux generated by the second inspection module to move the second inspection module over the platen surface to perform the second automated inspection operation.

Additional aspects are defined by the claims of this patent.

DETAILED DESCRIPTION

In apparatus, systems and methods in accordance with the present disclosure, inspection operations for workpieces that previously were performed in part or entirely manually are automated. As described further herein, inspection end effectors are mounted on linear motors that can be directed along paths across surfaces of workpieces as the inspection end effectors perform their inspection operations. The inspection end effectors and the linear motors are components of an inspection apparatus having a platen or a plate over which the linear motors travel. The inspection apparatus may be positioned proximate the surfaces of the workpieces by positioning apparatus at an inspection station. Once the inspection apparatus is in position proximate the workpieces, the linear motors are controlled to move over the plate and across the surfaces so that the inspection end effectors can perform their inspection operations on the workpiece.

Figure 1:
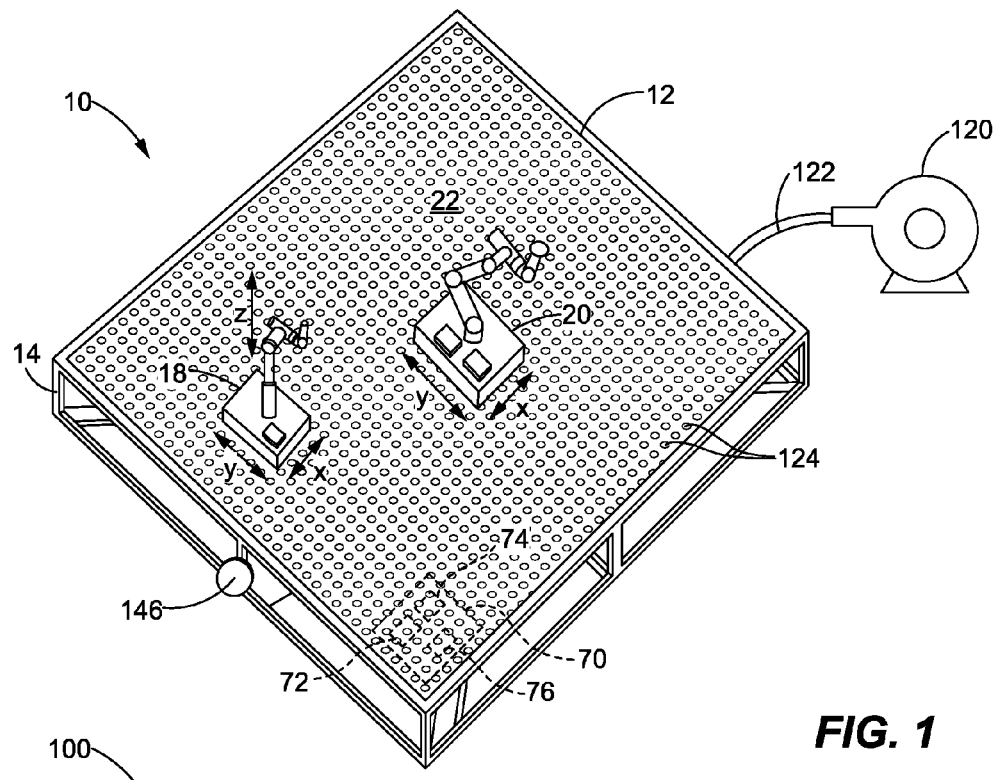
FIG. 1 is a perspective view of an embodiment of an inspection apparatus in accordance with the present disclosure for performing inspection operations on workpieces.

FIG. 1 illustrates one example of an inspection apparatus 10 in accordance with the present disclosure. The inspection apparatus 10 as shown includes a flat platen 12 fabricated from a magnetic material and mounted on a mounting bracket 14. The mounting bracket 14 may be a component of a positioning apparatus 136 (FIG. 5) that is illustrated and described further below with reference to FIG. 4. The inspection apparatus 10 further includes at least one inspection module 18 and/or at least one inspection module 20 disposed on a planar platen surface 22 of the platen 12. The inspection modules 18, 20 are configured with linear motors so that the inspection modules 18, 20 can be controlled to move in an X-direction and a Y-direction over the platen surface 22 so that inspection operations can be performed on a surface of a workpiece proximate to which the inspection apparatus is disposed.

Figure 2:
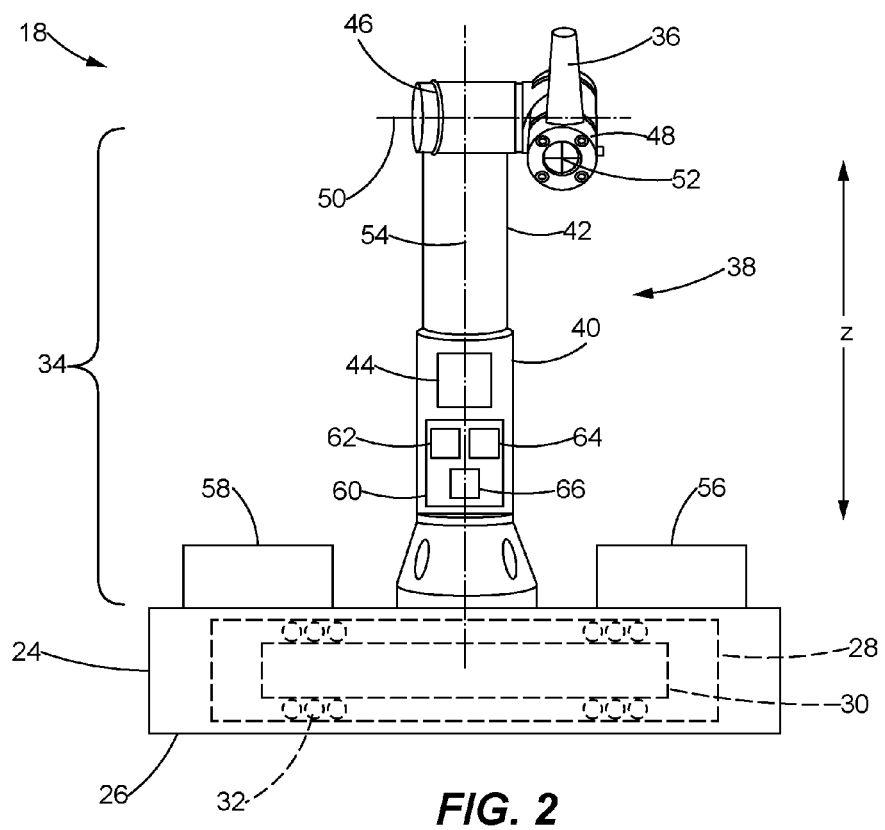
FIG. 2 is a side view of an embodiment of an inspection module in accordance with present disclosure of the inspection apparatus of FIG. 1.

An embodiment of the inspection module 18 is illustrated in greater detail in FIG. 2. In addition to moving over the platen surface 22, the inspection module 18 is configured to perform inspection operations on surfaces of workpieces. As illustrated, the inspection module 18 includes module base 24 having a planar bottom surface 26 that faces the platen surface 22 when the inspection module 18 is disposed on the platen 12. The module base 24 houses a linear motor 28 in the form of a Sawyer motor that includes a permanent magnet 30 and a phase winding 32. The permanent magnet 30 creates a magnetic force that biases the inspection module 18 toward the platen 12, and the phase winding 32 creates magnetic flux when a current runs through the wires of the winding 32. The magnetic flux will move the inspection module 18 over the platen surface 22 as described further below. In alternative embodiments, the permanent magnets 30 may be omitted, and the platen 12 may carry a permanent magnet that will interact with the magnetic flux created by the winding 32 in each module base 24 to move the inspection modules 18 over the platen surface 22. While Sawyer motors are illustrated and described herein, any appropriate linear motor capable of being controlled to provide two-dimensional motion of the inspection module 18 over the platen surface 22 is contemplated as having use in inspection apparatus 10 in accordance with present disclosure.

The inspection module 18 further includes an end effector positioning device 34 mounted on the module base 24 for positioning of an inspection end effector 36 of the inspection module 18 relative to the module base 24 and to a surface of a workpiece. The end effector positioning device 34 in the illustrated embodiment includes a telescoping arm 38 mounted to and extending from the module base 24. The telescoping arm 38 includes a lower tubular portion 40 and an upper tubular portion 42 slidably disposed within the lower tubular portion 40 so that the upper tubular portion 42 can slide in and out to retract and extend, respectively, the telescoping arm 38. The telescoping arm 38 may further include a linear actuator 44 operatively connected between the upper tubular portion 42 and either the lower tubular portion 40 or the module base 24 to control the position of the upper tubular portion 42 relative to the lower tubular portion 40. The linear actuator 44 may be any appropriate type of linear actuator for causing linear movement of the upper tubular portion 42, such as mechanical actuators using a screw or cam, a hydraulic or pneumatic actuators using pressure changes in liquid or air, respectively, to extend and retract the upper tubular portion 42, piezoelectric actuators, solenoid actuators, electro-mechanical actuators and the like.

The end effector positioning device 34 may further include two rotary actuators 46, 48 for controlling a rotational orientation of the inspection end effector 36. The first rotary actuator 46 may be attached at an end of the upper tubular portion 42 opposite the lower tubular portion 40 and the module base 24, and the second rotary actuator 48 may be mounted to an output shaft (not shown) of the first rotary actuator 46. The inspection end effector 36 may be operatively connected to an output shaft (not shown) of the second rotary actuator 48. The first rotary actuator 46 may operate to rotate the second rotary actuator 48 and the inspection end effector 36 about a first rotational axis 50, and the second rotary actuator 48 may operate to rotate the inspection end effector 36 about a second rotational axis 52.

In one embodiment, the first rotational axis 50 may be approximately parallel to the planar bottom surface 26 of the module base 24 and approximately perpendicular to an arm longitudinal axis 54 of the telescoping arm 38. The second rotational axis 52 may be approximately perpendicular to the first rotational axis 50. This arrangement allows three degrees of freedom for positioning in the inspection end effector 36 relative to the surface of the workpiece. Actuation of the linear actuator 44 to extend and retract the telescoping arm 38 to move the inspection end effector 36 toward or away from the workpiece parallel to the arm longitudinal axis 54 and in the Z-direction relative to the platen 12 (FIG. 1). Actuation of the rotary actuators 46, 48 adjusts the orientation of the inspection end effector 36 to correspond to contours of the surface of the workpiece. Of course, the arm longitudinal axis 54 and the rotational axes 50, 52 may have different relative orientations while still providing three degrees of freedom of movement to position the inspection end effector 36 as required for a particular implementation of the inspection apparatus 10.

As discussed above, the inspection end effector 36 may be operatively connected to the output shaft of the second rotary actuator 48. In the illustrated embodiment, the inspection end effector 36 is a visual inspection end effector that operates to visually record and evaluate the surface of the workpiece. The inspection end effector 36 is self-contained on the illustrated inspection module 18, so the inspection module 18 also includes a memory device 56 mounted thereon that may be operatively connected to the inspection end effector 36 by an appropriate connection. As the illustrated example, the inspection end effector 36 may obtain photographic or video images of the surface of the workpiece and transmit image data representing the images to the memory device 56 for temporary storage. The image data may be analyzed on board the inspection module 18 or transmitted to a remote device for analysis. Other types of inspection end effectors may be installed on the inspection module 18. In alternative embodiments, the inspection end effector 36 could be a sonographic inspection device, a thermographic inspection device, a radiographic inspection device, or any other appropriate inspection end effector for performing an inspection operation on the workpiece. In further alternative embodiments, various inspection end effectors 36 may be interchangeable on the end effector positioning device 34 such that a single inspection module 18 can be used to perform different types of inspection operations to perform a complete inspection on a workpiece.

The inspection module 18 as illustrated is a self-contained, autonomous component of the inspection apparatus 10 requiring power and control capabilities. Consequently, the inspection apparatus 10 may further include a power source 58 such as a battery pack mounted thereon. The power source 58 may be replaceable so that a charged power source 58 may be swapped in for a partially or fully spent power source 58 when necessary. In alternate implementations, the power source 58 may be permanently mounted to the inspection module 18 and rechargeable when necessary. The rechargeable power source 58 may have an appropriate connector (not shown) for attaching a recharging cord for supplying power to recharge the power source 58. The rechargeable power source 58 could alternatively be configured for wireless power transfer via a technique such as inductive coupling. The power from the power source 58 may be transmittable to the winding 32, the inspection end effector 36 and the actuators 44, 46, 48 via appropriate power transfer hardware and wiring.

The inspection module 18 may further include an inspection module controller 60 mounted thereon and configured to control the operations of the various components of the inspection module 18. The inspection module controller 60 may include a processor 62 for executing a specified program or programs that control and monitor various functions associated with the inspection module 18, such as operating the linear motor 28 to move the inspection module 18 and actuating the actuators 44, 46, 48 to position the inspection end effector 36. Although the processor 62 is shown, it is also possible and contemplated to use other electronic components such as a microcontroller, an application specific integrated circuit (ASIC) chip, or any other integrated circuit device. The inspection module controller 60 further includes a memory 64 that can include read only memory (ROM) for storing programs and random access memory (RAM) that serves as a working memory area for use in executing the programs stored in ROM. The inspection module controller 60 may also include a communications module 66 such as transceiver that is capable of communicating wirelessly with other control elements of the inspection apparatus 10, such as inspection module controllers 60 in other inspection modules 18 and an inspection apparatus controller 70 (FIG. 1) of the inspection apparatus 10. The inspection apparatus controller 70 may include a processor 72, a memory 74 having ROM and RAM, and a communications module 76 as described above. The inspection apparatus controller 70 is discussed in greater detail below. Though referred to herein as a single entities, the inspection module controller 60 and the inspection apparatus controller 70 may refer collectively to multiple control and processing devices across which the functionality of the inspection module 18 and the inspection apparatus 10 may be distributed.

Figure 3:
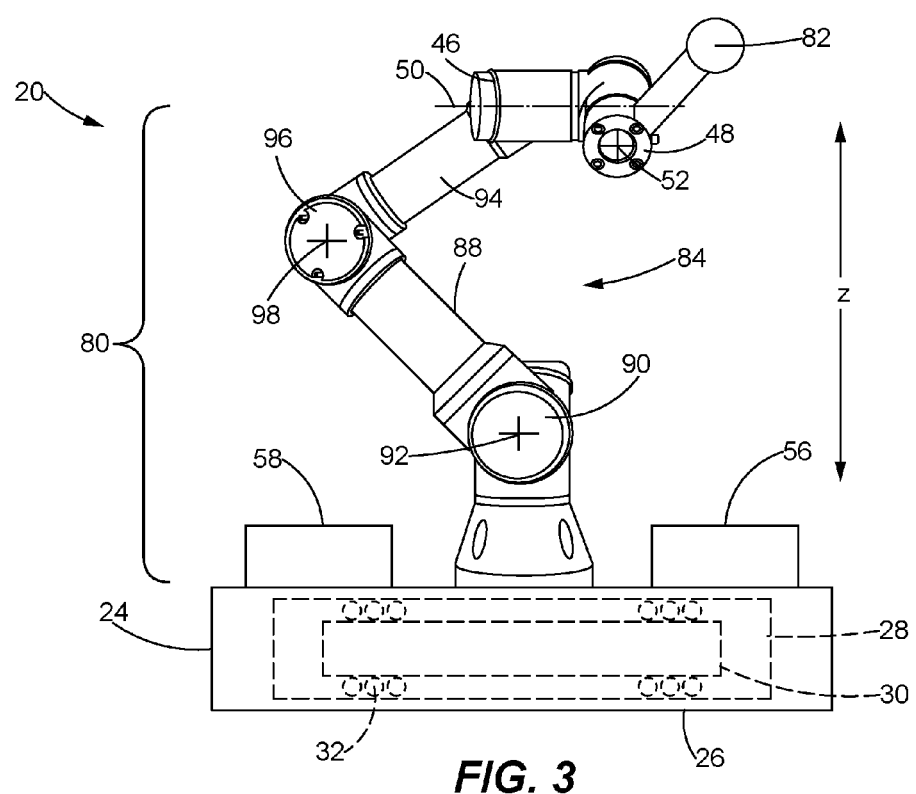
FIG. 3 is a side view of an alternative embodiment of an inspection module in accordance with present disclosure of the inspection apparatus of FIG. 1.

FIG. 3 illustrates the second embodiment of an inspection module 20 where similar components as previously discussed for the inspection module 18 are identified by the same reference numerals. The inspection module 20 has a generally similar configuration as the inspection module 18 including the module base 24 with the linear motor 28, an end effector positioning device 80 and an inspection end effector 82 in the form of a sensing end effector. The end effector positioning device 80 may be a robotic arm 84 mounted to the module base 24 by a mounting bracket 86. A lower arm 88 may be pivotally connected to the mounting bracket 86 by a first arm rotary actuator 90 for rotation of the lower arm 88 about a first arm rotational axis 92. An upper arm 94 may be pivotally connected to the lower arm 88 opposite the first arm rotary actuator 90 by a second arm rotary actuator 96 for rotation of the upper arm 94 relative to the lower arm 88 about a second arm rotational axis 98 that may be parallel to the first arm rotational axis 92.

The rotary actuators 46, 48 may be connected to the upper arm 94 and relative to each other in a similar manner as the connection in the end effector positioning device 34 as discussed above. Actuation of the rotary actuators 90, 96 can be coordinated by the inspection module controller 60 to extend and retract the arms 88, 94 to move the rotary actuators 46, 48 and the inspection end effector 82 in the Z-direction. The end effector positioning device 80 also allows for adjustment of the position of the inspection end effector 82 in either the X-direction or the Y-direction depending on the orientation of the inspection module 20. Similar to the discussion above, the rotary actuators 46, 48 provide two degrees of rotation of the inspection end effector 82 to orient the inspection end effector 82 relative to the surface of the workpiece.

The inspection end effector 82 in the illustrated embodiment may be a sensing end effector capable of sensing a property or properties of the surface. For example, the sensing end effector may be a distance sensor that is positioned to sense a distance to the surface of the workpiece. The sensed distance may be used by the inspection module controller 60 or the inspection apparatus controller 70 determine whether the platen 12 is too close to or too far from the surface to perform the required inspection operations such as painting or printing by appropriate medium dispensing end effectors. The sensed distance may also be communicated to other inspection modules 18, 20 to adjust their inspection end effectors 36, 82 to appropriate distances from the surface for performing their inspection operations.

The inspection end effector 82 could be other types of inspection devices such as a sonographic inspection device, a thermographic inspection device, a radiographic inspection device, or other type of non-destructive inspection device known in the art. For example, the inspection end effector 82 may be a sonographic end effector that is capable of producing and outputting sound waves and receiving echoes of the sound waves off the workpiece that are indicative of a structural property of the workpiece. The echoes received by the sonographic end effector may be converted to sonographic data that may be stored in the memory device 56 for later processing and analysis. However, the sonographic end effector or other such sensing end effectors may not require the memory device 56 described above, and it may be possible to omit the memory device 56 from either of the inspection modules 18, 20. It is further contemplated that any appropriate inspection end effector capable of performing non-destructive inspection and testing of the workpiece may be installed on either type of inspection module 18, 20.

The planar platen 12 of the inspection apparatus 10 of FIG. 1 may be adequate for performing many of the inspection operations on many of the workpieces on which the operations are performed. In some situations, it may be difficult due the geometry of the surface of the workpiece to efficiently perform the inspection operations with the planar platen 12. For example, the curvature of a fuselage of an aircraft may only allow a portion of the planar platen 12 to be disposed in close enough proximity to the surface of the fuselage to perform an inspection operation such as painting.

In such situations, it may be desirable to modify the geometry of the platen to be more complimentary to the shape of the workpiece.

Figure 4:
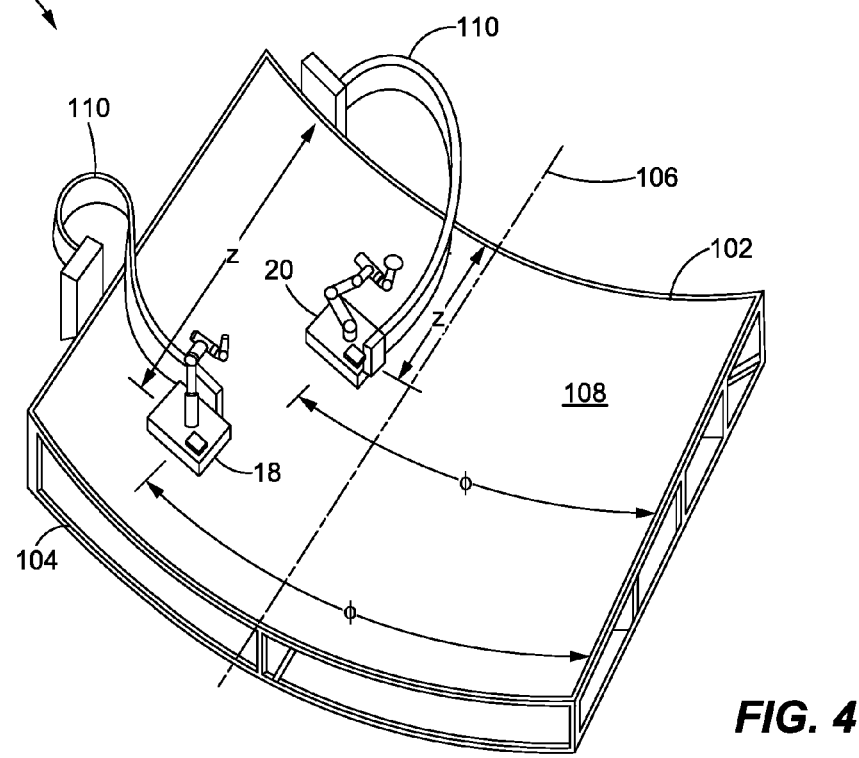
FIG. 4 is a perspective view of an alternative embodiment of an inspection apparatus in accordance with the present disclosure for performing inspection operations on surfaces of workpieces.

Referring to FIG. 4, an alternative embodiment of an inspection apparatus 100 having a curved platen 102 mounted on a mounting bracket 104 that conforms more closely to the shapes of workpieces upon which the inspection apparatus 100 will perform inspection operations. In the illustrated embodiment, the curved platen 102 is a hollow horizontal cylindrical segment having a constant radius of curvature R from a platen longitudinal axis 106. Locations on a platen surface 108 of the curved platen 102 may be identified using a cylindrical coordinate system. A radial distance ρ is a perpendicular distance from the platen longitudinal axis 106 to the point on the platen surface 108. The radial distance ρ is equal to the radius of curvature R for all points on the curved platen 102. An azimuth φ is an angle about the platen longitudinal axis 106 between a reference position, such as a corner of the curved platen 102, and the point on the platen surface 108. A height z is a distance along the platen longitudinal axis 106 from the reference position to the point on the platen surface 108. This convention may be used by the inspection apparatus controller 70 and/or the inspection module controllers 60 to control the movement of the inspection modules 18, 20 over the platen surface 108.

The inspection modules 18, 20 have generally the same configurations as described above, but with some modifications to adapt the inspection modules 18, 20 to the curved platen 102. The bottom surfaces 26 of the module bases 24 of the inspection modules 18, 20 may be curved instead of planar to correspond to the curvature of the platen surface 108. Also, though not required, the inspection modules 18, 20 may be more directly controlled by the inspection apparatus controller 70. The inspection modules 18, 20 may be more directly connected to the inspection apparatus 100 by tethers 110. The tethers 110 may contain wiring operatively connecting the inspection apparatus controller 70 to the various electrical components of the inspection modules 18, 20, including the windings 32 and the inspection end effectors 36, 82, for transmission of power, control signals and inspection data. With this arrangement, the inspection modules 18, 20 may not require some or all of the memory device 56, the power source 58 and the inspection module controller 60, and such components may be omitted. While use of the tethers 110 may simplify and reduce components of the inspection modules 18, 20, the tethers 110 may place constraints on the inspection module 18, 20 moving over the platen surfaces 22, 108 to avoid engaging and entangling the tethers 110.

Returning to FIG. 1, one or more of the inspection modules 18, 20 can move over the platen surface 22 by actuating the linear motors 28 in the module bases 24. A bearing system of the inspection apparatus 10 may provide a gap between the platen surface 22 and the bottom surfaces 26 of the module bases 24 to allow the inspection modules 18, 20 to glide over the platen surface 22 with minimal resistance due to friction. In one embodiment, the bearing system may be an air bearing wherein a pressurized air source 120, such as a pump, provides pressurized air through a conduit 122 to the platen 12. The pressurized air is discharged through a plurality of orifices 124 through the platen 12 that may be evenly spaced across the platen surface 22. The discharged air creates a layer of air between the platen surface 22 and the bottom surfaces 26 of the inspection modules 18, 20 despite the attractive force of the permanent magnets 30 biasing the inspection modules 18, 20 toward the platen surface 22. However, the attractive force is sufficient to maintain the inspection modules 18, 20 in close proximity to the platen surface 22 even through a 360° rotation of the platen 12. The air gap created by the discharged air allows the inspection modules 18, 20 to glide over the platen surface 22 in the X-direction, the Y-direction, or in a combination thereof, without friction acting against the movement of the inspection modules 18, 20. The air bearing system may be implemented in a similar manner in the curved inspection apparatus 100 of FIG. 3

In an alternative embodiment, the bearing system may be a roller bearing system allowing the inspection modules to roll over the platen surface 22. In the roller bearing system, roller bearings (not shown) may be installed in the bottom surfaces 26 of the module bases 24. The roller bearings partially extend below the bottom surfaces 26 and engage the platen surface 22 to create a constant air gap between the platen surface 22 and the bottom surfaces 26. The roller bearings will roll over the platen surface 22 with some amount of friction resisting the movement of the inspection modules 18, 20, but with less friction than would exist with surface-to-surface contact between the platen surface 22 and the bottom surfaces 26.

With the air gap established between the platen surface 22 and the bottom surfaces 26, the windings 32 of the linear motors 28 may be energized to move the inspection modules 18, 20. The magnetic flux generated by the windings 32 interacts with the permanent magnets 30 and the platen 12 to cause the inspection modules 18, 20 to glide over the platen surface 22 in the X-direction, the Y-direction, or in a combination thereof. The flow of current through the windings 32 may be controlled the inspection module controller 60 and/or the inspection apparatus controller 70 to move the inspection modules 18, 20 along predetermined paths. As the inspection modules 18, 20 move along the paths, the end effector positioning devices 34, 80 and the rotary actuators 46, 48 may be operated to change the position and orientation of the inspection end effectors 36, 82 as necessary to follow the contours of a surface of a workpiece. At the same time, the inspection end effectors 36, 82 may be operated to perform the corresponding inspection operations on the surface of the workpiece.

Figure 5:
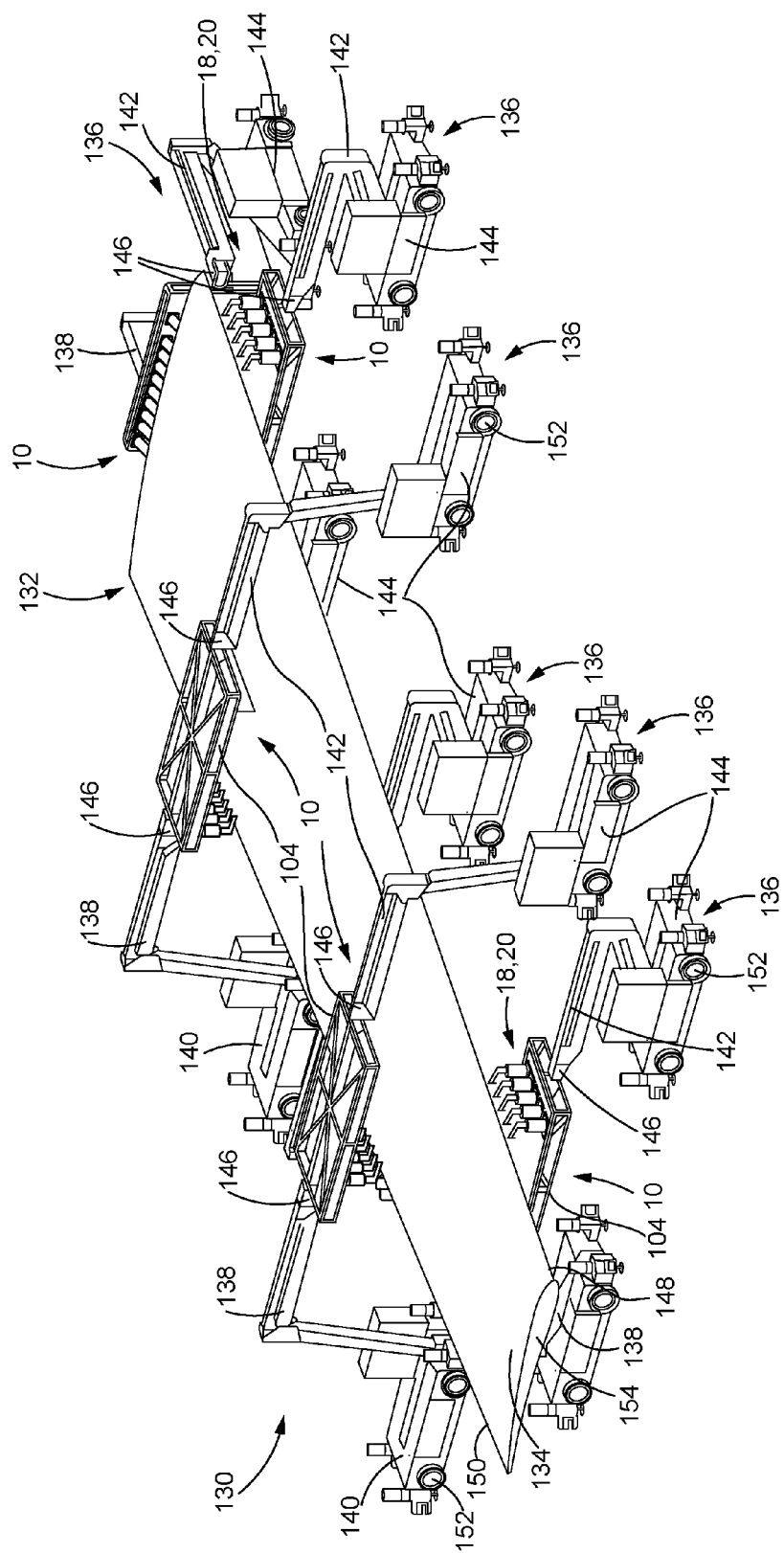
FIG. 5 is a perspective view of an embodiment of an inspection station in accordance with the present disclosure implementing a plurality of the inspection apparatus of FIG. 1.

FIG. 5 illustrates an example of the inspection station 130 at which a plurality of the inspection apparatus 10 may simultaneously perform inspection operations on a workpiece 132 in the form of an aircraft wing. The inspection station 130 may be particularly applicable for performing inspection operations on workpieces 132 having generally flat surfaces 134 or surfaces having relatively large radii of curvature so that a majority of the platen surface 22 of the planar platen 12 may positioned in close enough proximity to the workpiece 132 for the inspection modules 18, 20 to perform the inspection operations. The inspection apparatus 10 may be mounted on and carried by corresponding positioning apparatus 136 that may be capable of moving the inspection apparatus 10 into position proximate the workpiece 132 and around the inspection station 130.

In the illustrated embodiment, each positioning apparatus 136 is a movable gantry system having a first lift arm 138 connecting an end of the platen mounting bracket 14 to a first omnidirectional cart 140 (also known as an omni-cart 140), and a second lift arm 142 connecting the opposite end of the platen mounting bracket 14 to a second omnidirectional cart 144. The lift arms 138, 142 may be articulated so that each can be raised, lowered, extended or retracted independently of the other. Connections 146 of the lift arms 138, 142 to the platen mounting bracket 14 may provide multiple degrees of freedom to facilitate orienting the inspection apparatus 10 to any desired position. The inspection apparatus 10 may be rotatable by an appropriate rotary actuator (not shown) through 360° of rotation about an axis extending through the connections 146 to the lift arms 138, 142. This rotation may allow the inspection apparatus 10 to be disposed above, below or adjacent to the workpiece 132 with the platen surface 22 facing a corresponding portion of the surface 134 of the workpiece 132.

The connections 146 may allow one or more additional rotational degrees of freedom allowing the inspection apparatus 10 to pivot relative to the lift arms 138, 142. The additional rotational freedom may provide further adjustment of the orientation of the inspection apparatus 10 to match the contour of the surface 134 of the workpiece 132. For example, the top side of the surface 134 of the aircraft wing in FIG. 5 slopes downward as the surface 134 extends rearward from a leading edge 148 toward a trailing edge 150. The inspection apparatus 10 disposed above the surface 134 as shown in FIG. 5 are farther from the surface 134 proximate the trailing edge 150 than proximate the middle of the surface 134. The connections 146 allow the first lift arm 138 to lower the corresponding end of inspection apparatus 10 toward the trailing edge 150 while the second lift arm 142 maintains its position as the inspection apparatus 10 rotates downward. The connections 146 further facilitate orientation of the inspection apparatus 10 as shown with the rightmost positioning apparatus 136 in FIG. 5 to orient the inspection apparatus 10 facing a side of the workpiece.

The omni-carts 140, 144 facilitate movement of the entire positioning apparatus 136 and the inspection apparatus 10 relative to the workpiece 132 and around the inspection station 130. As shown in FIG. 5, the wheels 152 of the omni-carts 140, 144 are turned so that the omni-carts 140, 144 can move toward and away from the workpiece 132. This limited range of movement may be sufficient where the workpiece 132 is moved into and out of position in the inspection station 130, and in particular above or below the inspection apparatus 10. In other embodiments, the positioning apparatus 136 may be provided with a great range of motion by configuring all four wheels 152 of the omni-carts 140, 144 to rotate 90° about vertical axes from the illustrated positions. Once rotated, the omni-carts 140, 144 can move the positioning apparatus 136 and the inspection apparatus 10 perpendicular to the direction of movement shown in FIG. 5. This may allow the workpiece 132 to remain in place as the positioning apparatus 136 reposition the inspection apparatus 10 along the length of the workpiece 132 to perform the inspection operations at multiple locations along the workpiece 132. The positioning apparatus 136 can also drive past a wing tip 154 and take the inspection apparatus 10 out of proximity to the workpiece 132 when the inspection operations are completed.

With the increased mobility afforded by the positioning apparatus 136 as described, the inspection station 130 is not required to be restricted to a defined location within a facility. It may be possible to bring the inspection station 130 to the workpiece 132 and perform the inspection operations at that location, especially where the workpiece 132 is large and it may be impractical to move around the facility. Of course, in alternative implementations, the inspection station 130 may be established at a fixed location within a facility. It is also contemplated that the lift arms 138, 142 may be able to adequately position the inspection apparatus 10 without the added mobility provide by the omni-carts 140, 144. In such implementations, the omni-carts 140, 144 may be omitted and the lift arms 138, 142 may be mounted on a floor, platform or other permanent structure in a manner that will support the inspection apparatus 10 and the lift arms 138, 142 as the inspection operations are performed.

Figure 6:
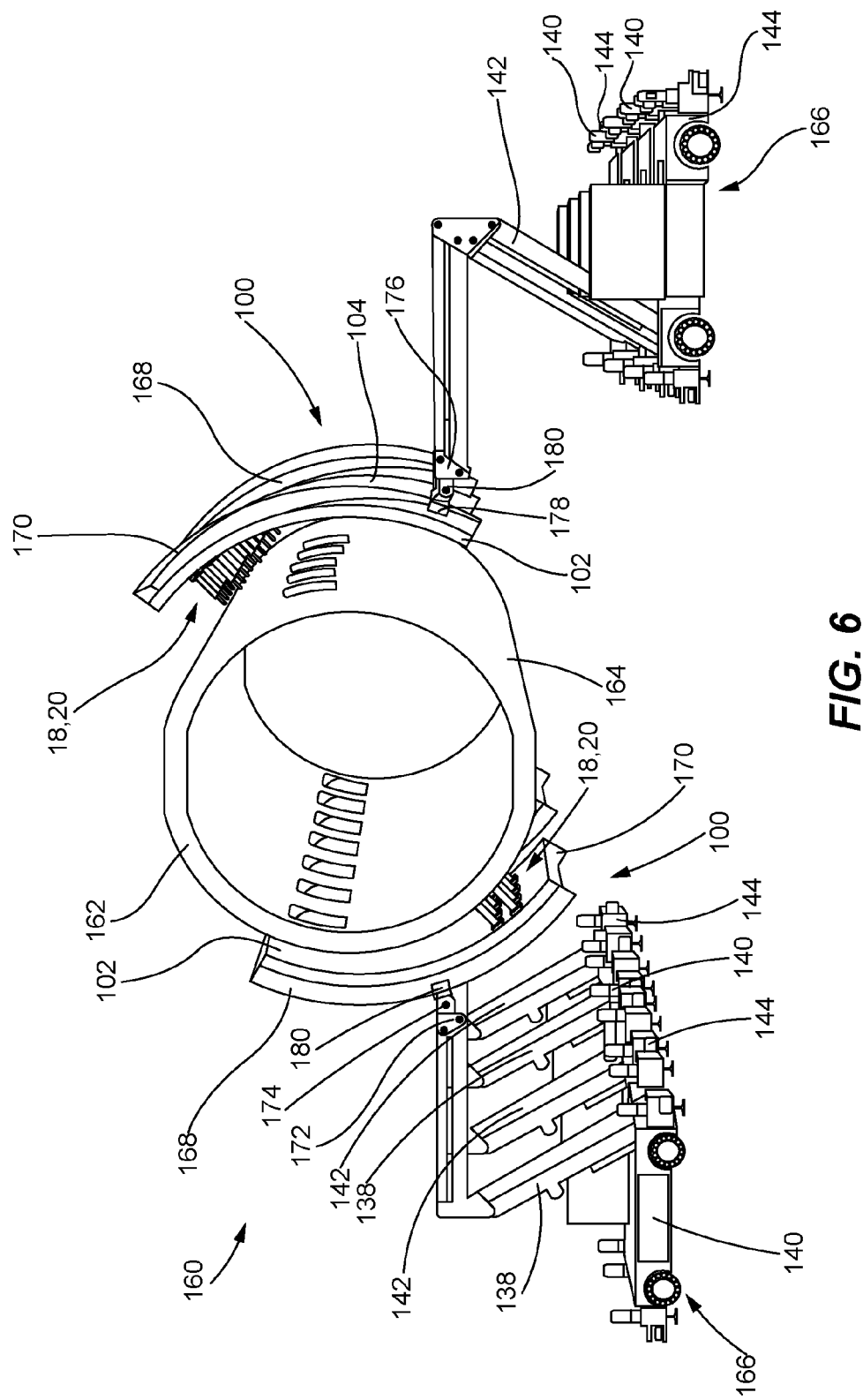
FIG. 6 is a perspective view of an alternative embodiment of an inspection station in accordance with the present disclosure implementing a plurality of the inspection apparatus of FIG. 4.

FIG. 6 illustrates an alternative embodiment of an inspection station 160 where inspection operations are performed using the inspection apparatus 100 with the curved platen 102 of FIG. 4. The inspection station 160 may have particular application for a workpiece 162 having a surface 164 with a high degree of curvature such as the airplane fuselage as illustrated. The inspection station 160 may have positioning apparatus 166 for the inspection apparatus 100 having lift arms 138, 142 and omni-carts 140, 144 that are substantially as described above with reference to the inspection station 130 of FIG. 5. However, the positioning apparatus 166 differs from the positioning apparatus 136 in the connection of the positioning apparatus 166 to the mounting bracket 104 of the inspection apparatus 100.

The mounting bracket 104 may include a first positioning rail 168 and a second positioning rail 170. The positioning rails 168, 170 have arcuate shapes that are complimentary to the concave outer surface of the curved platen 102 and have radii of curvature that are centered on the platen longitudinal axis 106 (FIG. 4). The first positioning rail 168 is received at a first connection 172 of the first lift arm 138 by a first guide bracket 174 and the second positioning rail 170 is received at a second connection 176 of the second lift arm 142 by a second guide bracket 178. Appropriate actuators (not shown) may operate to slide the positioning rails 168, 170 in the guide brackets 174, 178 to adjust the circumferential position of the inspection apparatus 100 relative to the workpiece 162. As shown in FIG. 6, the guide brackets 174, 178 retain the positioning rails 168, 170 of the inspection apparatus 100 on the left side of the figure at approximately a midpoint along the circumferential length of the positioning rails 168, 170 and the curved platen 102. For the inspection apparatus 100 on the right, the guide brackets 174, 178 retain the positioning rails 168, 170 proximate a lower edge of the curved platen 102. Consequently, while the lift arms 138, 142 and the omni-carts 140, 144 are in similar positions relative to the workpiece 162, the inspection apparatus 100 on the right is positioned higher on the surface 164 than the inspection apparatus 100 on the left.

The connections 172, 176 may each have a pivot shaft 180 with a rotational axis that is parallel to the platen longitudinal axis 106. The guide brackets 174, 178, and consequently the inspection apparatus 100, may be rotated about the pivot shaft 180 by an appropriate actuator (not shown). This additional degree of freedom of movement of the inspection apparatus 100 may further facilitate orienting the inspection apparatus 100 relative to the surface 164 of the workpiece 162. As with the inspection station 130, the lift arms 138, 142 may be able to adequately position the inspection apparatus 100 without the added mobility provide by the omni-carts 140, 144, and the omni-carts 140, 144 may be omitted and the lift arms 138, 142 may be mounted on a permanent structure. It is also contemplated that the inspection stations 130, 160 may be combined into a single inspection station providing both inspection apparatus 10, 100 so that the combined inspection station could perform inspection operations efficiently on workpieces having diverse surface contours.

Figure 7:
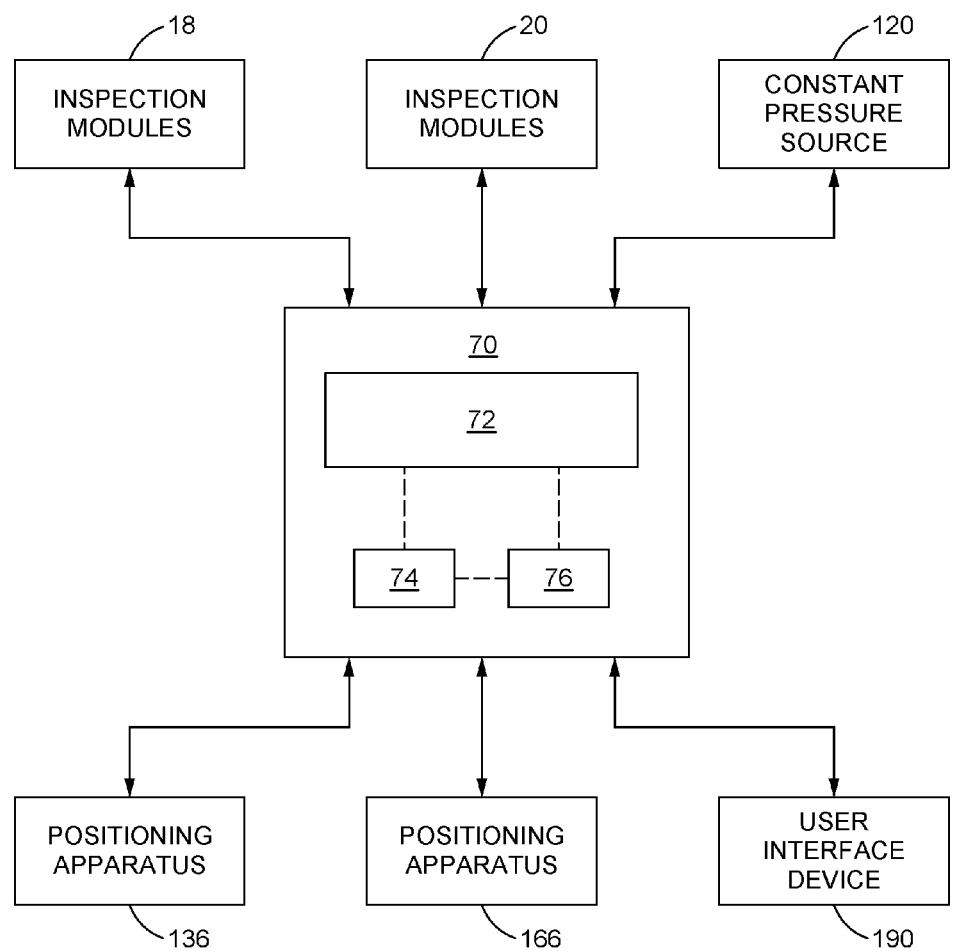
FIG. 7 is a schematic illustration of control elements of the inspection stations of FIGS. 5 and 6.

In one embodiment, the overall operations of the inspection stations 130, 160 may be controlled and coordinated centrally at the inspection apparatus controller 70. Referring to FIG. 7, the inspection apparatus controller 70 may be communicatively linked to the other functional components of the inspection stations 130, 160 directly or wirelessly by the communications module 76. For example, the inspection apparatus controller 70 may communicate with the inspection modules 18, 20 with instruction regarding paths to use in traversing the platen surfaces 22, 108, and where to position and when to actuate the inspection end effectors 36, 82 to perform their inspection operations. The inspection modules 18, 20 may communicate information to the inspection apparatus controller 70 such as sensor signals containing information from the sensing end effectors, inspection data stored at the memory device 56, and power levels at the power source 58. The inspection apparatus controller 70 may also communicate with the pressurized air source 120 regarding when to begin and when to cease outputting pressurized air to the platens 12, 102.

To the extent that the operations of the positioning apparatus 136, 166 are automated, the inspection apparatus controller 70 may transmit control signals to the control components of the positioning apparatus 136, 166 to move the inspection apparatus 10, 100 into position proximate one of the workpieces 132, 162. The positioning apparatus 136, 166 may execute the commands and respond by transmitting messages indicating whether the inspection apparatus 10, 100 are in position. When the inspection processes are complete, the inspection apparatus controller 70 may transmit further control signals to the positioning apparatus 136, 166 to withdraw the inspection apparatus 10, 100 from the workpieces 132, 162 so the workpieces 132, 162 can be moved to the next processing station, or the inspection stations 130, 160 can be relocated to the next workpieces 132, 162 on which inspection operations will be performed The inspection stations 130, 160 may further include a user interface device 190 that may allow operators at the inspection stations 130, 160 to communicate with the inspection apparatus controller 70. The operators may enter information at the user interface device 190 that will be transmitted and stored at the inspection apparatus controller 70. Such information may include multi-inspection module workpiece inspection routines, travel paths for the inspection modules 18, 20 to traverse while performing their inspection operations, portions of the travel paths during which the inspection end effectors 36, 82 will be actuated to perform their inspection operations, geometric information for the surfaces 134, 164 of the workpieces 132, 162, inspection apparatus positing information to be used by the positioning apparatus 136, 166 to position and orient the inspection apparatus 10, 100 proximate the surfaces 134, 164 of the workpieces 132, 162, and the like. The information may be input manually by the operator, or the user interface device 190 may include input ports for connecting peripheral devices such as storage devices or portable computing devices, or establishing network connections to local area networks (LANs), wide area networks (WANs) or other remote networks that may download the information.

The transmitted information may be stored at the inspection apparatus controller 70 and transmitted in real time to the inspection modules 18, 20, the pressurized air source 120 and the positioning apparatus 136, 166 as the inspection operations are being performed. Alternatively, the information may be distributed from the inspection apparatus controller 70 to the other control components as the information is received. Such distribution of information may allow the devices to perform their functions independently and without relying on the inspection apparatus controller 70 or another centralized control device to coordinate the operations being performed at the inspection stations 130, 160.

The user interface device 190 may also receive data from the inspection apparatus controller 70 relating to the execution of the inspection operations at the inspection stations 130, 160. The execution data may include information such as inspection operation status information generated by the various components during the inspection operations and indicative of progress of the inspection operations as they are occurring, inspection operation error or defect information indicating the occurrence of events such as errors in performing the inspection operations, detected quality exceptions and the like. The user interface device 190 may display the status information at a display device, store the information, transmit the information to other devices or systems, or use the data for any other appropriate processing and evaluation of the inspection operations.

The arrangement of components and the exchange of information described in relation to FIG. 7 are exemplary only. The execution and control of the inspection operations performed at the inspection stations 130, 160 may be centralized, distributed or combined in hybrid control structures between the control elements discussed herein and other control elements as necessary to efficiently perform the inspection operations. Such alternative control strategies are contemplated as having use in methods and apparatus in accordance with the present disclosure.

INDUSTRIAL APPLICABILITY

Figure 8:
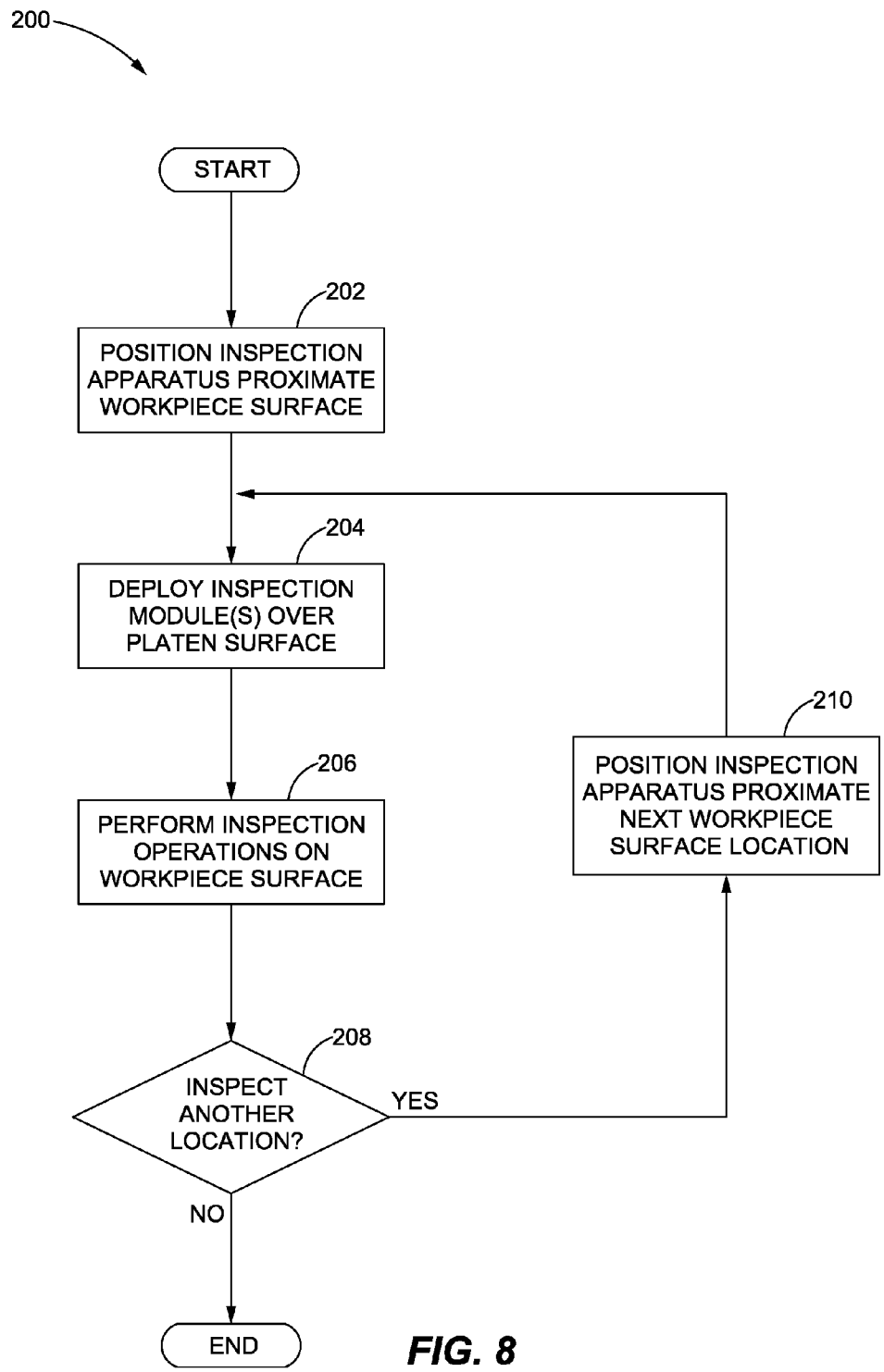
FIG. 8 is a flow diagram of an automated inspection operation routine in accordance with the present disclosure that may be performed by the inspection apparatus of FIGS. 1 and 4.

The operation of the components described above is illustrated in FIG. 8 that presents an exemplary automated inspection operation routine 200 for performing an inspection operation or inspection operations on a surface of a workpiece. The inspection station 130 with the inspection apparatus 10 performing inspection operations on the surface 134 of the workpiece 132 are referenced in the following discussion of the routine 200, however the routine 200 may be implemented at the inspection station 160 with the inspection apparatus 100, or a hybrid inspection station having both types of inspection apparatus 10, 100. Such variations and implementations are contemplated herein.

The automated inspection operation routine 200 may begin at a block 202 where the inspection apparatus 10 is positioned proximate the surface 134 of the workpiece 132. As discussed above, the inspection apparatus controller 70 or a controller of the positioning apparatus 136 may store geometric information for the workpiece 132 and other appropriate information for operating the positioning apparatus 136 to position the inspection apparatus 10 at a predetermined location on the surface 134 of the workpiece 132. At the block 202, the information is retrieved and used by the positioning apparatus 136 move to the workpiece 132 if necessary, and position and orient the inspection apparatus 10 proximate the location on the surface 134 with the platen surface 22 facing the surface 134. As discussed further below, positioning the inspection apparatus 10 may be an iterative process where the position of the inspection apparatus 10 is evaluated to determine if the inspection modules 18, 20 can perform respective inspection operations. If the inspection apparatus 10 is not in the proper position, the position and/or orientation is adjusted based on the information from the evaluation until the inspection operations can be performed on the surface 134.

Once the inspection apparatus 10 is properly positioned, control may pass to a block 204 where at least one inspection module 18, 20 is deployed over the platen surface 22. Path information stored at the inspection apparatus controller 70 and/or the inspection module controllers 60 may define the route the inspection modules 18, 20 traverse over the platen surface 22 and past the surface 134. The path information is used by one of the controllers 60, 70 to cause current to be transmitted to the windings 32 in the linear motor 28 to begin moving the inspection module 18, 20 along the path.

In one exemplary implementation, one of the inspection modules 18 with an inspection end effector 36 will inspect the surface 134 of the workpiece 132, and the inspection module 18 may follow a serpentine path and be deployed to at a corner of the platen 12 to begin traversing the path. In other embodiments, multiple inspection modules 18, 20 each having the same type of inspection end effector 36, 82 may inspect the surface 134, with each inspection module 18, 20 traveling along a different path. The paths may be coordinated and integrated so that the inspection modules 18, 20 can traverse the paths simultaneously and collision free, and the entire surface 134 is inspected when the inspection modules 18, 20 reach the ends of their respective paths. Further embodiments may incorporate the inspection modules 18, 20 having different types of inspection end effectors 36, 82. A first inspection module 18 may have an inspection end effector 36 configured to obtain photographic and/or video images of the surface 134 that are analyzed to identify any surface defects on the workpiece 132. The first inspection module 18 may be deployed over a path as described above. A second inspection module 20 may have an inspection end effector 82 for performing inspection of the surface 134 and/or structure of the workpiece beneath the surface 134. For example, the inspection end effector 82 may be a thermographic device creating a three-dimensional thermal image of the workpiece 132. Other combinations of inspection modules 18, 20 and inspection operations are contemplated, and in each case the inspection modules 18, 20 are deployed to the starting positions of their respective paths and traverse their respective paths to perform a complete inspection of the workpiece 132.

With the inspection module(s) 18, 20 deployed along their respective travel paths, control may pass to a block 206 where the inspection module(s) 18, 20 perform respective inspection operations. Control signals may be transmitted to the inspection end effectors 36, 82 causing the inspection end effectors 36, 82 to obtain images of the surface 134 as the inspection modules 18, 20 travel along respective paths. Control signals transmitted to the inspection end effectors 36, 82 will cause the inspection end effectors 36, 82 to perform the inspection operations such as sonographic, thermographic, and/or radiographic inspections as the inspection modules 18, 20 travel along respective paths. The inspection operations will continue being performed according to the instructions in the control signals until the inspection modules 18, 20 reach the ends of the paths.

When all of the inspection operations have been performed by the inspection modules 18, 20 at the location on the surface 134, control may pass to a block 208 where the inspection apparatus controller 70 or the inspection module controllers 60 determine whether the inspection apparatus 10 is directed to perform inspection operations at another location on the surface 134 of the workpiece 132. If the inspection apparatus 10 is instructed to another location, control may pass to a block 210 where the inspection apparatus 10 is repositioned proximate the next location of the surface 134 of the workpiece 132. The process for repositioning the inspection apparatus 10 may be similar to that described above in relation to the block 202 for positioning the inspection apparatus 10 at the first location on the surface 134. If the inspection apparatus controller 70 or the inspection module controllers 60 determine that the inspection apparatus 10 has completed performing inspection operations of the surface 134 at the block 208, the routine 200 may terminate, after which the routine 200 may begin execution again when another workpiece 132 is to be inspected at the inspection station 130.

Figure 9:
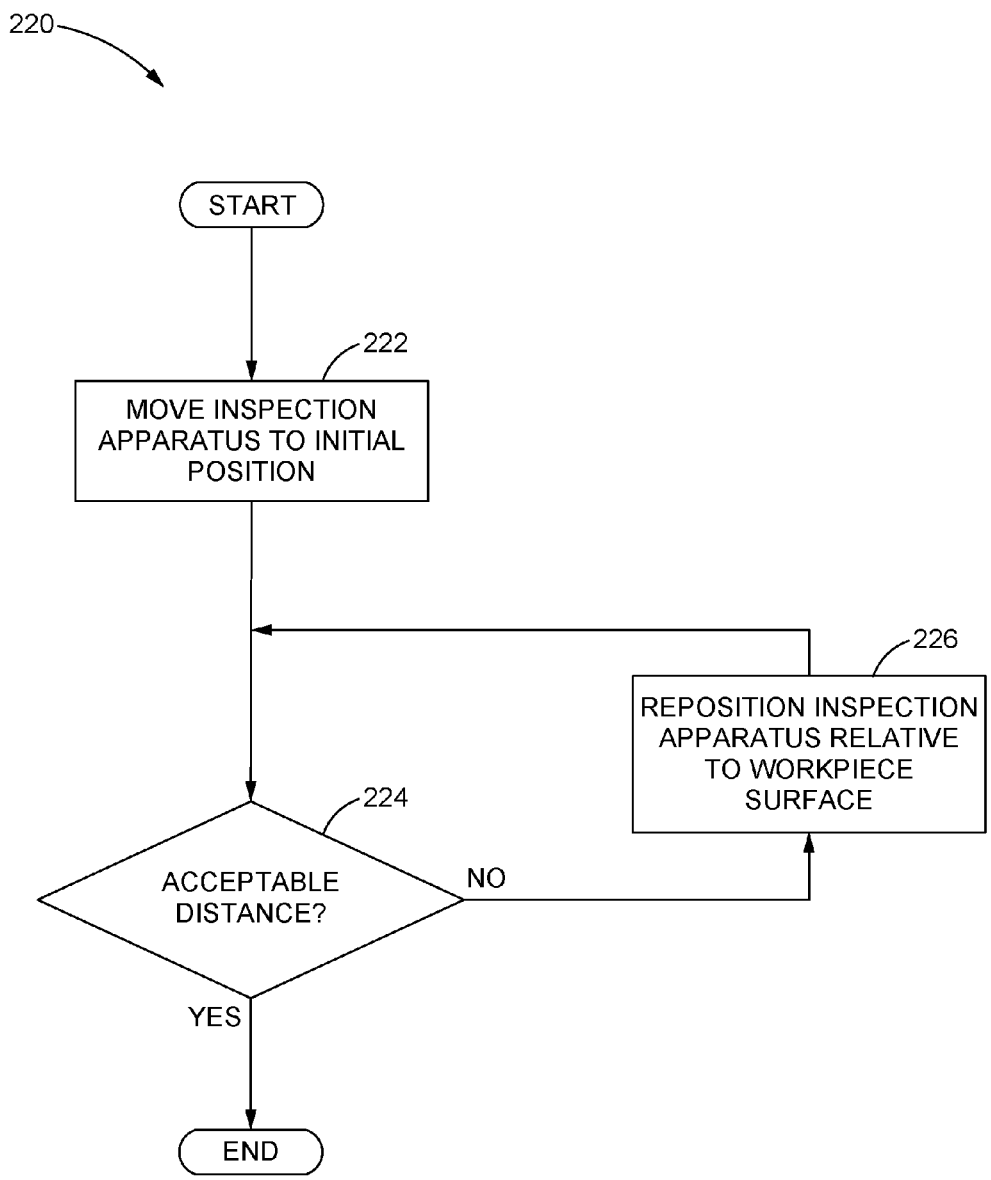
FIG. 9 is a flow diagram of an inspection apparatus positioning routine in accordance with the present disclosure that may be performed within the automated inspection operation routine of FIG. 8.

As discussed above, the process for positioning the inspection apparatus 10 performed at blocks 202 and 210 of the routine 200 may be iterative processes. An embodiment of an inspection apparatus positioning routine 220 is illustrated in FIG. 9. The routine 200 may be executed within the block 202 of the automated inspection operation routine 200 of FIG. 8. The routine 220 may begin at a block 222 where the inspection apparatus 10 is moved to an initial position proximate the surface 134 of the workpiece 132. The geometric information and other positioning information stored at the inspection apparatus controller 70 or the controller of the positioning apparatus 136 may be used to position the inspection apparatus 10 at a predetermined initial position proximate the location on the surface 134 of the workpiece 132 with the platen surface 22 facing the surface 134.

After the inspection apparatus is moved to the initial position, control may pass to a block 224 where the inspection apparatus controller 70 or an inspection module controller 60 determines whether the inspection apparatus 10 is positioned within an acceptable range of distances from the surface 134. If the inspection apparatus 10 is too close to the surface 134, the inspection modules 18, 20 could come into contact with the surface 134 and cause damage to the workpiece 132 or mar or inadvertently alter a finish applied to the surface 134. If the inspection apparatus 10 is too far from the surface 134, the inspection modules 18, 20 may not be close enough to the surface 134 to perform the inspection operations with the required quality. The distance to the surface 134 may be determined by deploying one or more of the inspection modules 20 with inspection end effectors 82 in the form of distance sensors. The inspection modules 20 may be caused to traverse a predetermined distance inspection path and sense the distance to the surface 134 at multiple points along the path. The distance sensors may transmit distance sensor signals to the controllers 60, 70 containing values corresponding to the distances to the surface 134 at the various points along the distance inspection path.

If values from the distance sensor signals are less than a predetermined minimum surface distance or greater than a maximum surface distance, all or a portion of the inspection apparatus 10 is not disposed at an acceptable distance from the surface 134. In this condition, control may pass to a block 226 where the inspection apparatus 10 is repositioned relative to the surface 134 based on the values in the distance sensor signals. If the entire inspection apparatus 10 is too close to or too far from the surface 134, the positioning apparatus 136 will move the inspection apparatus 10 closer to or away from the surface 134 as dictated by the distance sensor signal values by a distance that should place the inspection apparatus 10 within the range of acceptable surface distances. Where portions of the inspection apparatus 10 are too close to the surface 134 and other portions are within the surface distance range, the positioning apparatus 136 may be controlled to rotate the close portions of the inspection apparatus 10 away from the surface 134 by an amount that should move the portions within the acceptable distance range between maximum and minimum surface distances. Conversely, portions of the inspection apparatus 10 that are too far from the surface 134 may be rotated toward the surface 134 by the positioning apparatus 136 by an amount that should move the portions within the acceptable distance range between maximum and minimum surface distances. After the position adjustment of the inspection apparatus 10, control may pass back to the block 224 to evaluate whether the inspection apparatus 10 in the readjusted position within the range of acceptable distances.

If the values from the distance sensor signals are greater than the predetermined minimum surface distance and less than the maximum surface distance, the inspection apparatus 10 is disposed at an acceptable distance from the surface 134. In this condition, the inspection apparatus 10 is properly positioned relative to the surface 134. With the inspection apparatus 10 properly positioned, the routine 220 may terminate until the inspection apparatus 10 is again positioned proximate a surface 134 of a workpiece 132.

Figure 10:
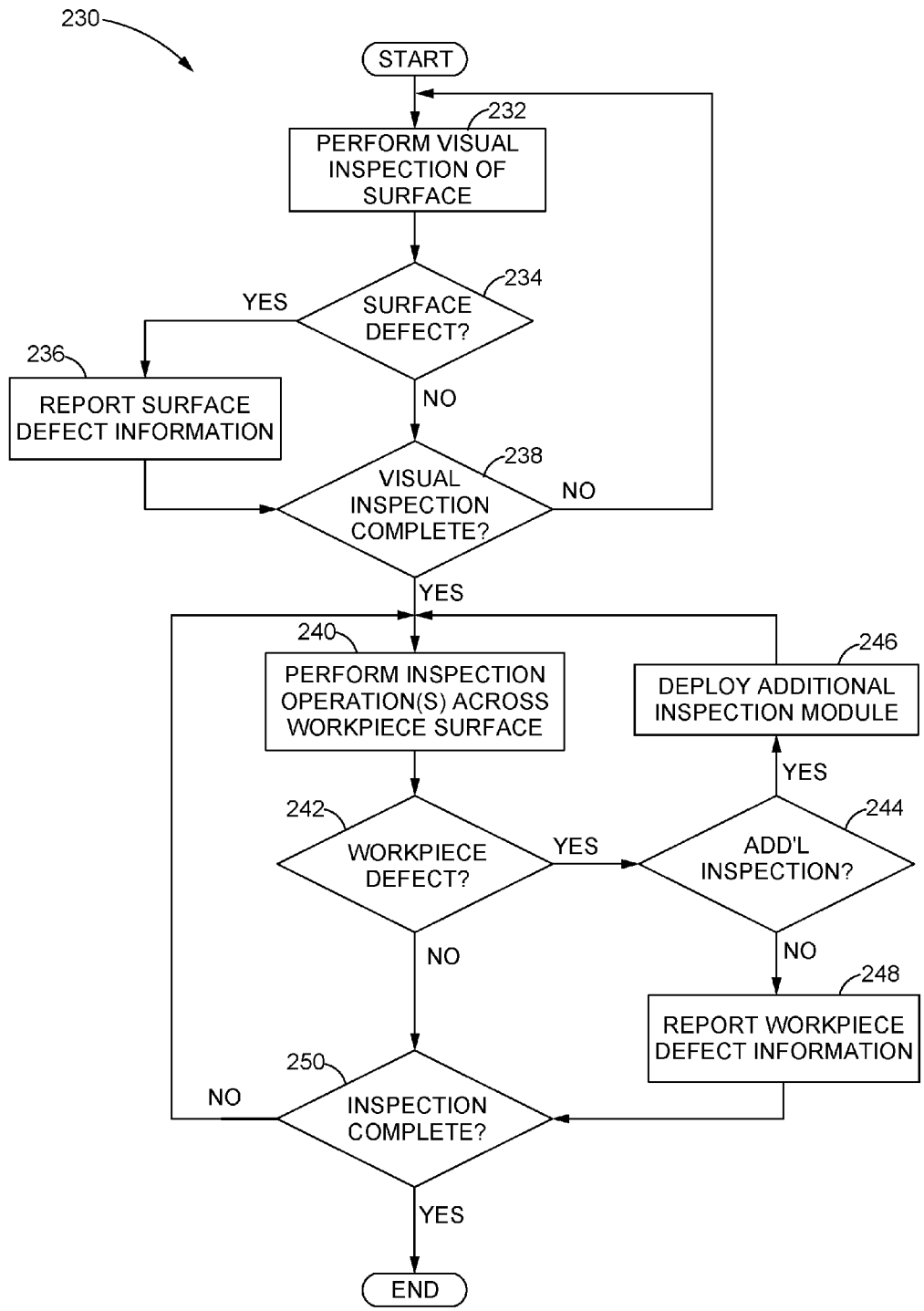
FIG. 10 is a flow diagram of an inspection apparatus performance routine in accordance with the present disclosure that may be performed within the automated inspection operation routine of FIG. 8.

FIG. 10 illustrates an inspection operation performance routine 230 that may be executed within the block 206 of the routine 200. In the present example, the routine 230 contemplates inspecting the workpiece 132 using one or more inspection modules 18, 20 having inspection end effectors 36, 82. The routine 230 may include an initial visual inspection of the surface 134 followed by inspection of the surface 134 and/or the structure of the workpiece 132 beneath the surface 134 performed by other types of inspection end effectors 36, 82. The routine 230 may begin at a block 232 where surface conditions of the surface 134 are visually inspected to determine whether any surface defects are present that may need to be repaired before the workpiece 132 can pass the inspection. Similar to the discussion above, one or more inspection modules 18, 20 having inspection end effectors 36, 82 may be deployed along predetermined surface condition inspection paths. While traversing the inspection paths, the inspection end effectors 36, 82 may detect the presence or absence of surface defects, such as cracks, chipped paint or other surface coating, missing or improperly installed bolts or rivets, and the like, at multiple points on the surface 134 along the inspection path.

The inspection end effectors 36, 82 may transmit image data signals to the controllers 60, 70 as the inspection modules 18, 20 traverse the path or in a batch after the inspection modules 18, 20 store the data in the memory devices 56 while completing the inspection path. Periodically during the visual inspection at the block 232, or after the inspection modules 18, 20 complete travel along the inspection paths, control may pass to a block 234 where the controllers 60, 70 or technicians at the user interface device 190 analyze the image data to determine whether surface defects are present on the surface 134. If surface defects are detected, control may pass to a block 236 to report information regarding the surface defects. The surface defect information may be transmitted to the user interface device 190 or other appropriate device or system to trigger the performance of maintenance or other corrective operations that may be required to place the surface 134 in condition to pass the inspection of the workpiece 132. In alternative embodiments of the routine 230 and the inspection apparatus 10, one or more of the inspection modules 18, 20 may be equipped with finishing end effectors that can sand, scrape, grind, brush, sweep or otherwise operate on the surface 134 to correct the surface defect(s). In such embodiments, the controllers 60, 70 may be configured to deploy the inspection modules 18, 20 with the finishing end effectors to repair the surface 134 in response to detecting the surface defect(s).

After the reporting is performed, and/or after the surface defect(s) are corrected by the finishing end effectors if available, or if no surface defects were detected from the image data at the block 234, control may pass to a block 238 to determine whether the visual inspection of the surface 134 of the workpiece 132 is complete. If the inspection modules 18, 20 with the inspection end effectors 36, 82 are still traversing the inspection paths, or if additional inspection modules 18, 20 have not yet been deployed, and the visual inspection is not complete, control may pass back to the block 232 to continue the visual inspection of the surface 134 to detect if additional surface defects are present on the surface 134.

If the visual inspection is complete at the block 238, control may pass to block 240 to proceed with performing the inspection operations on the workpiece 132 with inspection end effectors 36, 82 on the inspection modules 18, 20. As discussed earlier with reference to the inspection operations in the routine 200, the inspection may be performed by a single inspection module 18, 20 traversing an inspection path covering the entire portion of the surface 134 to be inspected. In other embodiments, multiple inspection modules 18, 20 may inspect the surface 134, with each inspection module 18, 20 traveling along a different path. The paths may be integrated so that the entire portion of the surface 134 is inspected when the inspection modules 18, 20 reach the ends of their respective paths. The inspection end effectors 36, 82 may perform the same type of inspection, or multiple different types of inspections are performed simultaneously. In the latter case, the inspection modules 18, 20 may perform one type of inspection, and then switch inspection end effectors 36, 82 to retrace the inspection paths while performing different types of inspection. Alternatively, a first group of inspection modules 18, 20 may perform the first type of inspection across the surface 134, followed by a second group of inspection modules 18, 20 performing different types of inspections across the surface 134 along the inspection path.

The inspection end effectors 36, 82 may transmit inspection data signals to the controllers 60, 70 as the inspection modules 18, 20 traverse the inspection paths or in a batch after the inspection modules 18, 20 store the data in the memory devices 56 while completing the inspection paths. Periodically during the inspection operations at the block 240, or after the inspection modules 18, 20 complete travel along the inspection paths, control may pass to a block 242 where the controllers 60, 70 or technicians at the user interface device 190 analyze the inspection data to determine whether workpiece defects are present in the workpiece 132. The workpiece defects can include, for example, any condition that may compromise the structural integrity of the workpiece 132. Such workpiece defects may include internal cracks in the workpiece 132, variations in the thickness of a coating on the surface 134, material density variations, voids and pores, foreign object damage (FOD), and the like. Composite parts formed using composite materials may have particular defect conditions such as incomplete bonding, disbonding or delamination between composite layers.

If workpiece defects are detected at the block 242, control may pass to a block 244 determine whether additional inspection operations are available to further analyze the detected workpiece defect. Depending on the type of defect detected, a further inspection operation may verify that the defect does in fact exist, or provide further information about the defect. For example, a defect first identified by a sonographic inspection may be confirmed or further analyzed by performing a thermographic or radiographic inspection. In other implementations, an initial rapid scanning inspection may be performed at a low resolution to identify potential defects in the workpiece 132. If workpiece defects are found during the initial scan, the resolution may be increased on the inspection end effectors 36, 82, or separate inspection modules 18, 20 may be deployed to perform a higher resolution inspection at the location(s) of the detected workpiece defect(s).

If additional inspection operations are available for the detected workpiece defect at the block 244, control may pass to a block 246 to deploy the inspection modules 18, 20 that can perform the additional inspection operations. With the additional inspection modules 18, 20 deployed, control may pass back to the block 240 to perform the additional inspection operations either across the entire surface 134 of the workpiece 132 or at the specific locations where the workpiece defect(s) has(have) been identified. If no additional inspection operations are available at the block 244, control may pass to a block 248 to report information regarding the workpiece defects. The workpiece defect information may be transmitted to the user interface device 190 or other appropriate device or system to trigger the performance of maintenance or other corrective operations that may be able to place the workpiece 132 in condition to pass the inspection. Of course, some workpiece defects may structurally compromise the workpiece 132 such that no corrective actions can be performed that will allow the workpiece 132 to pass the inspection.

After the reporting of the workpiece defect(s) is performed at the block 248, or if no workpiece defects were detected from the inspection data at the block 242, control may pass to a block 250 to determine whether the inspection operations on the workpiece 132 are complete. If the inspection modules 18, 20 with the inspection end effectors 36, 82 are still traversing the inspection paths, or if additional inspection modules 18, 20 have not yet been deployed, and the sensor inspection operations are not complete, control may pass back to the block 240 to continue the sensor inspection operations on the workpiece 132 to detect if additional workpiece defects are present. If the inspection operations are complete at the block 250, the routine 230 may terminate until the next workpiece 132 is ready for inspection.

The inspection operation performance routine 230 is exemplary, and alternative routines 230 for performing a complete inspection of the workpiece 132 are contemplated. For example, the visual and sensor inspection operations described above may be performed simultaneously. Alternatively, the visual inspection operations may be performed after the sensor inspection operations. Further alternatives for inspecting a workpiece inspection that may reduce the cycle time for performing the inspections and increase the accuracy of the workpiece inspections as compared to manual or semi-automated inspection processes may be implemented in inspection operation performance routines 230 in accordance with the present disclosure.

While the preceding text sets forth a detailed description of numerous different embodiments, it should be understood that the legal scope of protection is defined by the words of the claims set forth at the end of this patent. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims defining the scope of protection.

It should also be understood that, unless a term was expressly defined herein, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to herein in a manner consistent with a single meaning, that is done for sake of clarity only so as to not confuse the reader, and it is not intended that such claim term be limited, by implication or otherwise, to that single meaning.

What is claimed is:

1. An inspection apparatus for performing automated inspection operations across a surface of a workpiece, the inspection apparatus comprising:
    a platen fabricated from a magnetic material and having a platen surface; and
    a first inspection module disposed on the platen surface and having a first inspection end effector, wherein the first inspection module generates a first magnetic field that biases the first inspection module toward the platen, and is operable to generate a first magnetic flux to control movement of the first inspection module over the platen surface to perform a first automated inspection operation across the surface of the workpiece.

2. The inspection apparatus in accordance with claim 1, wherein the first inspection end effector comprises a visual inspection end effector that obtains images of the surface of the workpiece as the first inspection module moves over the platen surface and transmits image data representing the images.

3. The inspection apparatus in accordance with claim 1, wherein the first inspection end effector comprises a sensing end effector that senses values of a structural property of the workpiece as the first inspection module moves over the platen surface and transmits sensing data representing the values of the structural property.

4. The inspection apparatus in accordance with claim 3, wherein the sensing end effector performs one of a sonographic inspection, a thermographic inspection and a radiographic inspection across the surface of the workpiece.

5. The inspection apparatus in accordance with claim 1, comprising a second inspection module disposed on the platen surface and having a second inspection end effector, wherein the second inspection module generates a second magnetic field that biases the second inspection module toward the platen, and is operable to generate a second magnetic flux to control movement of the second inspection module over the platen surface to perform a second automated inspection operation across the surface of the workpiece.

6. The inspection apparatus in accordance with claim 5, wherein the second automated inspection operation is a different automated inspection operation than the first automated inspection operation.

7. The inspection apparatus in accordance with claim 5, wherein the first magnetic flux controls movement of the first inspection module through a first inspection path and the second magnetic flux controls movement of the second inspection module through a second inspection path, and wherein the first inspection module and the second inspection module traverse the first inspection path and the second inspection path, respectively, simultaneously and without colliding.

8. A method of performing automated inspection operations across a surface of a workpiece, the method implemented using a first inspection module having a first inspection end effector and being disposed on a platen surface of a platen fabricated from a magnetic material, wherein the first inspection module generates a first magnetic field biasing the first inspection module toward the platen surface, the method comprising:

deploying the first inspection module over the platen surface using a first magnetic flux generated by the first inspection module; and performing, using the first inspection end effector, a first automated inspection operation.

9. The method in accordance with claim 8, wherein the first inspection end effector is a visual inspection end effector, the method further comprising:

obtaining at the visual inspection end effector images of the surface of the workpiece as the first inspection module moves over the platen surface; and transmitting from the visual inspection end effector image data representing the images.

10. The method in accordance with claim 8, wherein the first inspection end effector is a sensing end effector, the method comprising:

sensing at the sensing end effector values of a structural property of the workpiece as the first inspection module moves over the platen surface; and transmitting sensing data representing the values of the structural property.

11. The method in accordance with claim 10, wherein the sensing end effector performs one of a sonographic inspection, a thermographic inspection and a radiographic inspection across the surface of the workpiece.

12. The method in accordance with claim 8, wherein the method is further implemented using a second inspection module having a second inspection end effector and being disposed on the platen surface of the platen, wherein the second inspection module generates a second magnetic field biasing the second inspection module toward the platen surface, the method comprising:

deploying the second inspection module over the platen surface using a second magnetic flux generated by the second inspection module; and performing, using the second inspection end effector, a second automated inspection operation.

13. The method in accordance with claim 12, wherein the second automated inspection operation is a different automated inspection operation than the first automated inspection operation.

14. The method in accordance with claim 12, comprising:

controlling the first magnetic flux to move the first inspection module through a first inspection path; and controlling the second magnetic flux to move the second inspection module through a second inspection path simultaneously with controlling the first magnetic flux to move the first inspection module through the first inspection path, wherein the first inspection module and the second inspection module traverse the first inspection path and the second inspection path, respectively, without colliding.

15. The method in accordance with claim 12, comprising:

controlling the first magnetic flux to move the first inspection module through a first inspection path; and controlling the second magnetic flux to move the second inspection module through the first inspection path after controlling the first magnetic flux to move the first inspection module through the first inspection path.

16. An inspection station for performing automated inspection operations across a surface of a workpiece, the inspection station comprising:

a platen fabricated from a magnetic material and having a platen surface;

a first inspection module disposed on the platen surface and having a first inspection end effector, wherein the first inspection module generates a first magnetic field that biases the first inspection module toward the platen, and is operable to generate a first magnetic flux to control movement of the first inspection module over the platen surface to perform a first automated inspection operation across the surface of the workpiece;

a first inspection module controller coupled in communication with the first inspection module, the first inspection module controller configured to control the first magnetic flux generated by the first inspection module to move the first inspection module over the platen surface to perform the first automated inspection operation;

a second inspection module disposed on the platen surface and having a second inspection end effector, wherein the second inspection module generates a second magnetic field that biases the second inspection module toward the platen, and is operable to generate a second magnetic flux to control movement of the second inspection module over the platen surface to perform a second automated inspection operation across the surface of the workpiece; and a second inspection module controller coupled in communication with the second inspection module, the second inspection module controller configured to control the second magnetic flux generated by the second inspection module to move the second inspection module over the platen surface to perform the second automated inspection operation.

17. The inspection station in accordance with claim 16, wherein the first inspection end effector comprises a visual inspection end effector that obtains images of the surface of the workpiece as the first inspection module moves over the platen surface and transmits image data representing the images, and the second inspection end effector comprises a sensing end effector that senses values of a structural property of the workpiece as the first inspection module moves over the platen surface and transmits sensing data representing the values of the structural property.

18. The inspection station in accordance with claim 17, wherein the first magnetic flux controls movement of the first inspection module through a first inspection path and the second magnetic flux controls movement of the second inspection module through a second inspection path, and wherein the first inspection module and the second inspection module traverse the first inspection path and the second inspection path, respectively, simultaneously and without colliding.

19. The inspection station in accordance with claim 16, wherein the first magnetic flux controls movement of the first inspection module through a first inspection path, and wherein the second magnetic flux controls movement of the second inspection module through the first inspection path after the first inspection module begins movement through the first inspection path.

20. The inspection station in accordance with claim 19, wherein the first inspection module controller is configured to detect a workpiece defect at a workpiece defect location of the workpiece as the first inspection module moves through the first inspection path, and wherein the second inspection module controller is configured to control the second magnetic flux to move the second inspection module to the workpiece defect location in response to the first inspection module controller detecting the workpiece defect of the workpiece.

\* \* \* \* \*